United States Patent [19]

Razi

[11] Patent Number: 5,254,131
[45] Date of Patent: Oct. 19, 1993

[54] NON-SLIP SURGICAL FORCEPS HAVING A BRACKET

[76] Inventor: Dean Razi, 5804 Cruiser Way, Tampa, Fla. 33615

[21] Appl. No.: 914,514

[22] Filed: Jul. 17, 1992

[51] Int. Cl.5 .............................................. A61B 17/42
[52] U.S. Cl. .................................................... 606/208
[58] Field of Search ............... 606/210, 211, 206, 207, 606/208

[56] References Cited

U.S. PATENT DOCUMENTS

| | | | |
|---|---|---|---|
| 3,140,715 | 7/1964 | Whitton, Jr. et al. | 606/210 |
| 3,392,727 | 7/1968 | Hanlon | 606/210 |
| 5,019,091 | 5/1991 | Porat et al. | 606/210 |

FOREIGN PATENT DOCUMENTS 2919271 11/1980 Fed. Rep. of Germany ...... 606/210

*Primary Examiner*—Jerome L. Kruter
*Attorney, Agent, or Firm*—Walter J. Monacelli

[57] ABSTRACT

The device described herein comprises a surgical forceps designed to prevent slipping of the tips of the forcep jaws, to avoid injury to the surgeon's thumb or finger and to provide non-slip grip of a patient's blood vessels and tissues. Originally such forceps had no provision for preventing the slipping of the forceps jaws. Then a pin or tiny rod was fixed vertically to the inside surface of one jaw of the forcep and a receptive opening in the other jaw positioned to receive the pin and thereby prevent slipping of the tips of the jaws away from each other and thus allowing a firm, non-slipping grip on a blood vessel and tissue and allowing the surgeon to use his other hand to manipulate a needle for suturing. Unfortunately the surgeon occasionally places a thumb or finger over the opening and when the pin is pushed through the opening, the pin sometimes pierces the flesh on the thumb or finger. In the improved forceps described herein, a first jaw of the forceps has a U-shaped bracket attached thereto, with the open portion facing the second jaw so that when the jaws are brought together, the open portion of the bracket receives and holds the second jaw so that slipping of one jaw over the other is prevented.

9 Claims, 2 Drawing Sheets

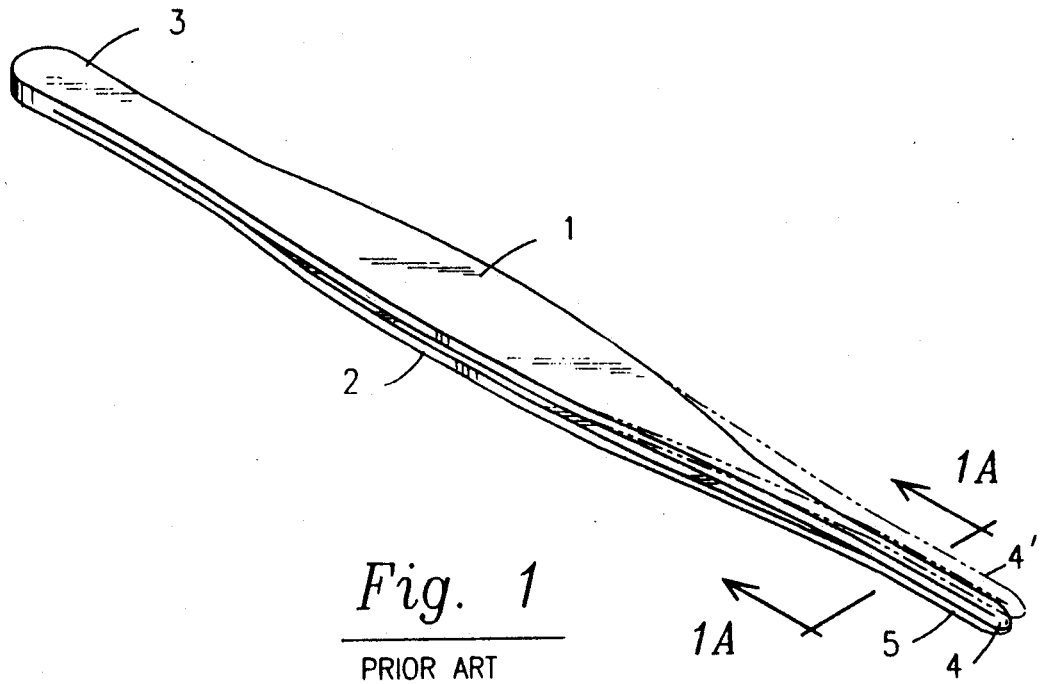
Fig. 1
PRIOR ART
Fig. 1A
PRIOR ART
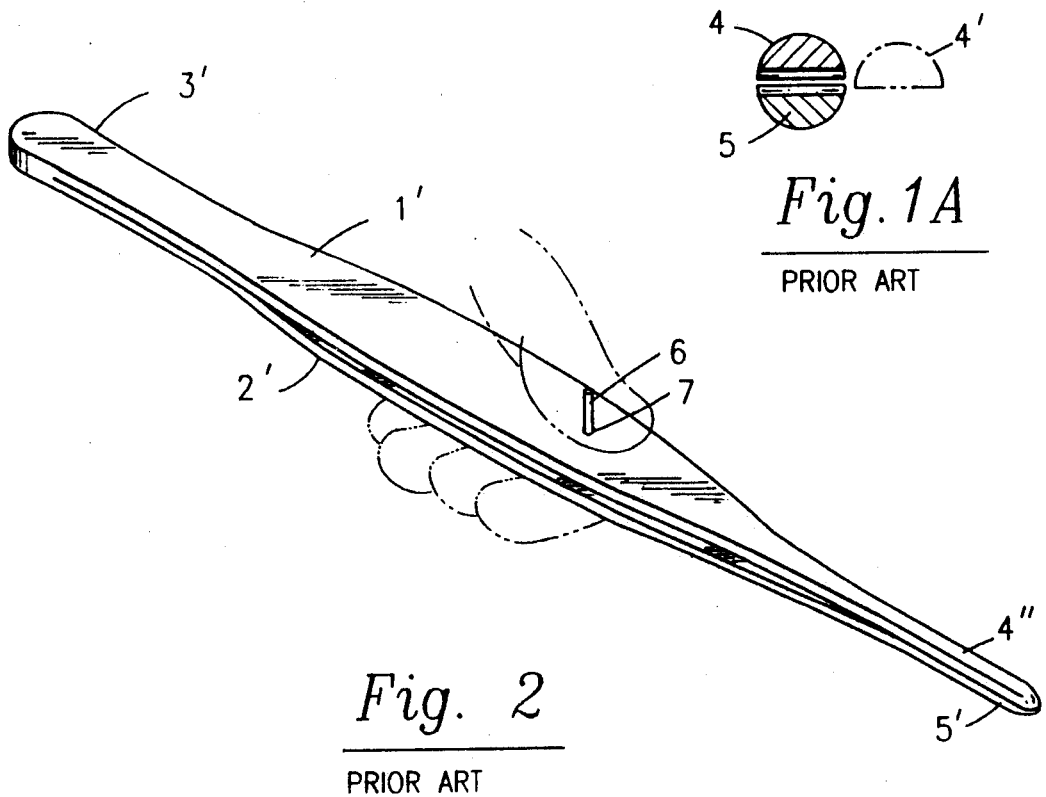
Fig. 2
PRIOR ART

NON-SLIP SURGICAL FORCEPS HAVING A BRACKET

BACKGROUND OF THE INVENTION

1. Field of the Invention

This invention relates to a surgical forceps which prevents slippage of one forceps jaw over the other jaw. More specifically it relates to surgical forceps which avoid the use of a pin inside one jaw adapted to be inserted in an opposing opening in the other jaw whereby slippage of the jaws is prevented by the positioning of the pin in the opening, which sometimes causes injury to the surgeon's thumb or finger when positioned over the opening. Still more specifically it relates to surgical forceps which has a bracket on one jaw of the forceps, this bracket having a shape which partially surrounds and embraces the other jaw of the forceps when the two jaws of the forceps are forced together, whereby the bracket prevents slipping of one jaw over the other. Still more specifically the bracket means for preventing slipping of one jaw over the other prevents injury to the surgeon's thumb or finger.

2. State of the Prior Art

Surgical forceps are known for holding tissue and blood vessels with one hand while the surgeon's other hand manipulates a needle and suturing thread to suture a patient's wound. An early type of forceps has no provision to prevent slippage of the tip of one of the forcep jaws over the other jaw particularly when tissue or a blood vessel is gripped between the tips. An improvement over this type of forceps comprises a forceps which has a pin or tiny rod extending perpendicularly from the inside of a first forceps jaw and extending toward the second or other forceps jaw. When the two jaws of the forceps are brought together, the pin becomes inserted in an opening in the second jaw positioned to receive the pin. The pin needs to be long enough that it extends beyond the outer surface of the second jaw since the initial positioning of the pin in the opening needs to be done while the jaws are a substantial distance from each other and the tissue or blood vessel is not yet firmly gripped by the jaws. Since the surgeon is concentrating on the blood vessels and tissue of the patient's wound, he often accidentally places a thumb or finger over the opening and when the pin extends beyond the opening, it may pierce the skin of the surgeon's thumb or finger. In addition to the discomfort and pain caused while the surgeon is trying to concentrate on the suturing operation, it is particularly dangerous in this age of aids and HIV infection to have commingling of the patient's and the surgeon's blood.

It is therefore most desirous to have a means for preventing slipping of the forceps jaws over each other and also to effect this by a means which will not cause the injury described above.

OBJECTIVES

It is an object of this invention to provide a surgeon's forceps which will not have the jaws twist while holding tissue or a blood vessel therebetween.

It is also an object of this invention to have such a surgeon's forceps which will also not cause any injury to the surgeon's thumb or finger.

Other objects will become obvious upon reading the detailed description of the invention as given hereinafter.

SUMMARY OF THE INVENTION

In accordance with the present invention, these objectives are met by the forceps of this invention which had a different means for preventing the twisting of one forceps jaw over the other when the forceps is holding tissue or a blood vessel therebetween. Instead of the pin described above, the restriction against twisting of one jaw over the other is a U-shaped bracket fixed on one jaw in such a manner that the open portion faces the other jaw and when the jaws are brought together, this bracket embraces the other jaw and prevents the jaws from twisting from or over each other. The spacing of the two arms of the U-shaped bracket is the same or close to the width of the jaw at the point where it will be embraced by the bracket. The bracket may vary in structure but will provide the two arms which will securely embrace the opposing jaw when the tips of the two jaws are brought together with or without tissue or a blood vessel therebetween. Preferably this bracket is made by bending a rectangular, oblong or circular flat plate into the U-shape which will embrace the opposing jaw. This U-shaped bracket is fixed to the first jaw, either to the side of the jaw away from the second jaw or, when the second jaw at that point is sufficiently spaced from the first jaw, the bracket may be fixed to the inside of the first jaw or that side facing the second jaw.

In addition to the flat plate type described above the bracket may actually be made with open spaces in the rectangular, oblong or circular structures referred to above, and may actually comprise a rigid wire or rod bent circumferentially in the various rectangular, oblong or circular shapes. Then when these are bent in the U-shape, they will provide brackets which will restrict movement of the second jaw when the bracket is rigidly fixed to the first jaw in a position whereby the bracket will embrace the second jaw when the tips of the jaws are brought together.

It is further contemplated that the bracket may be modified to the extent that the first jaw may serve as the connecting bottom of the U-shaped bracket. In such case the two arms may be welded or otherwise fixed so that the arms will extend toward the second jaw so that the second jaw may be embraced between the two arms fixed to the first jaw. In such case a portion of the jaw will serve as the bottom of the U-shaped bracket and serving to hold the two extending arms which will embrace the second jaw.

PREFERRED SPECIFIC EMBODIMENT

The description of the apparatus of this invention is facilitated by reference to the accompanying drawings.

FIG. 1 is a perspective view of an early prior art surgical forceps.

FIG. 1A is a cross-sectional view of this prior art forceps taken at line IA—IA of FIG. 1.

FIG. 2 is a perspective view of the prior art forceps currently being used.

Figure 3:
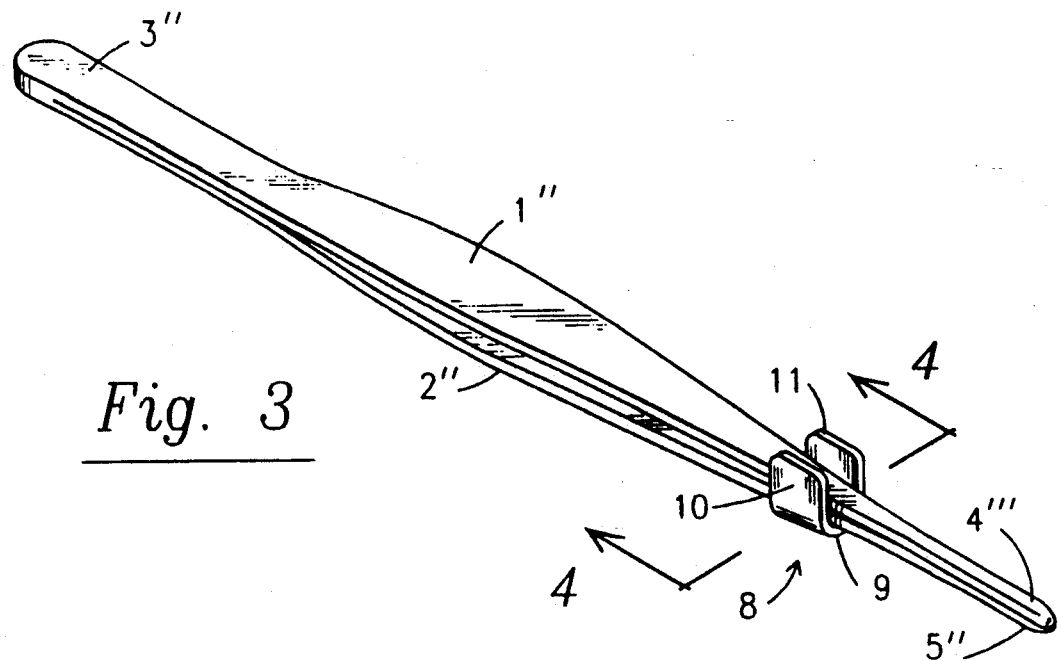
FIG. 3 is a perspective view of a preferred modification of the improved surgical forceps.

In the prior art forceps of FIG. 1 jaws 1 and 2 are joined at juncture 3 in such a manner that the jaws will separate an appropriate distance upon release of pressure on jaws 1 and 2. When tissue or a blood vessel is held between the jaw tips 4 and 5, these tips tend to twist away from each other as shown by the phantom position 4' of tip 4 and as shown in the cross-sectional view of FIG. 1A.

In the prior art forceps shown in FIG. 2, a pin 6 has been affixed to jaw 2' and extends through an opening 7 in jaw 1'. As shown in phantom the surgeon's thumb may be positioned above opening 7 and may be injured by pressing against pin 6.

FIG. 3 shows the improved forceps of this invention in which bracket 8 is affixed to jaw 2" so that jaw 1" is received in the open space between bracket arms 10 and 11. This space is such that jaw 1" at that point fits snugly between arms 10 and 11 and are prevented thereby from twisting over one another. In another modification arms 10 and 11 may be without bottom 9 and arms 10 and 11 may be welded or otherwise affixed to the sides of jaw 2. In such case jaw 2 will serve as the bottom of bracket 8 and serve to join the lower ends of arms 10 and 11.

Figure 4:
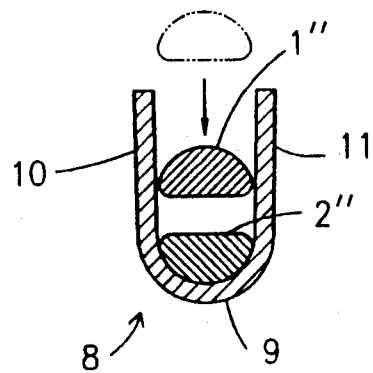
FIG. 4 is a cross-sectional view taken at line 4—4 of FIG. 3.

In the cross-sectional view of FIG. 4 the bottom 9 is shown as rounded. This bottom may also be flat and preferably its shape conforms to the shape of the lower surface of jaw 2". In FIG. 4 the phantom shape at the top shows the position of arm 1" before the jaws 1" and 2" are pressed toward each other to catch tissue or a blood vessel.

Figure 5:
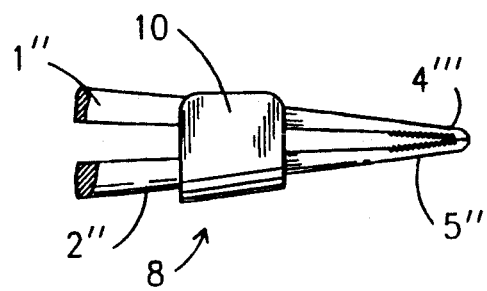
FIG. 5 is a partial side view of the forceps of FIG. 4.

FIG. 5 shows a side view of bracket 8 with arm 10 receiving arm 1" when it is pressed downward so that tip 4'" will meet tip 5". As shown more clearly in FIG. 4, the jaws are contained and not allowed to twist from each other.

Figures 6, 7:
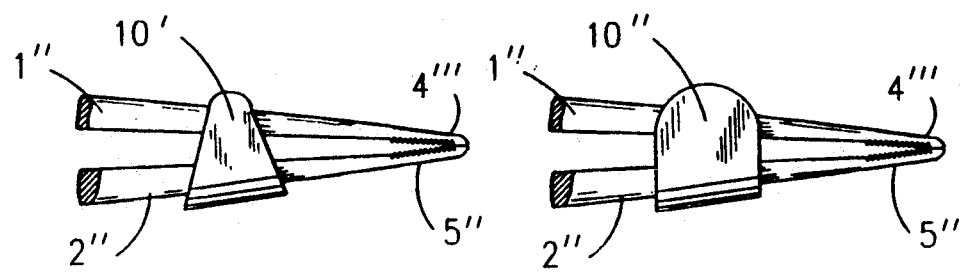
FIG. 6 is a partial side view of another modification of the forceps of this invention.
FIG. 7 is a partial side view of still another modification of the forceps of this invention.

FIGS. 6 and 7 show different shapes of arm 10' that may be used in other modifications of bracket 8. In other modifications contemplated these arms may have open spaces within the outer configurations so long as there are portions of the arms which will restrain the jaws from twisting away from each other.

The bracket described above is positioned between the midpoint of the length of the jaws and preferably approximately at a point distanced from the tip of the jaw between about one-fourth and one eighth of the length of the forceps.

Regardless of the exact shape of the bracket the important feature is that the jaw which is to be embraced by the bracket fits snugly between the arms of the bracket so as to prevent the twisting described.

While certain features of this invention have been described in detail with respect to various embodiments thereof, it will of course be apparent that other modifications can be made within the spirit and scope of this invention and it is not intended to limit the invention to the exact details shown above except insofar as they are defined in the following claims.

The invention claimed is:

1. A surgical forceps comprising:

(a) a first jaw having a length and shape suitable for surgical purposes and having a first end and a second end;

(b) a second jaw having an exterior surface having a shape and length similar to that of the first jaw and having a first end and a second end, the second end of the first jaw being joined to the second end of the second jaw in such a manner that the first end of each jaw will be spaced a slight distance from each other when there is no pressure applied to bring them together;

(c) a bracket having a bottom with two opposing sides and two arms, said bottom connecting said two arms extending parallel to each ocher and from said opposing sides of said bottom and having an open space therebetween, said arms extending in the same direction from said bottom having an open space therebetween said bracket being affixed to an exterior surface the second jaw with the arms extending toward and enclosing said first jaw and and provide means for receiving said first in jaw in the space between said arms whereby when said first jaw is positioned between said arms, said first jaw will be able to twist from said second jaw.

2. The forceps of claim 1 in which the center of said bracket is positioned between the midpoint of the length of said second jaw and a point spaced a distance from said second end of said second jaw of one eighth of the length of said second jaw, said length of said second jaw being the distance between said first end and said second end of said second jaw.

3. The forceps of claim 1 in which said bracket is positioned from the tip of the second jaw a distance between one fourth and one eighth of the length of said second jaw.

4. The forceps of claim 1 in which said bracket comprises a rigid metal rectangular strip bent in the shape of a U with the two arms extending parallel and toward the first jaw.

5. The forceps of claim 1 in which said bracket comprises two rigid metal arms welded to said second jaw whereby the adjacent portion of said jaw serves as the bottom connecting said two arms.

6. The forceps of claim 1 in which said bracket comprises a rigid metal rectangular strip bent in the shape of a U with the two arms extending parallel and toward the first jaw.

7. The forceps of claim 4 in which said bracket is positioned from the tip of the second jaw a distance between one fourth and one eighth of the length of said second jaw.

8. The forceps of claim 5 in which said bracket is positioned from the tip of the second jaw a distance between one fourth and one eighth of the length of said second jaw.

9. The forceps of claim 6 in which said bracket is positioned from the tip of the second jaw a distance between one fourth and one eighth of the length of said second jaw.

* * * * *

UNITED STATES PATENT AND TRADEMARK OFFICE
CERTIFICATE OF CORRECTION

PATENT NO. : 5,254,131
DATED : October 19, 1993
INVENTOR(S) : Dean Razi

It is certified that error appears in the above-identified patent and that said Letters Patent is hereby corrected as shown below:

Col. 4, line 24, after "will" insert "not".

Signed and Sealed this

Twenty-ninth Day of March, 1994

Attest:

BRUCE LEHMAN

Attesting Officer      Commissioner of Patents and Trademarks